(12) United States Patent
Arduini et al.

(10) Patent No.: US 8,518,015 B2
(45) Date of Patent: Aug. 27, 2013

(54) COUPLING DEVICE AND USE THEREOF

(75) Inventors: Arduino Arduini, San Giovanni Teatino (IT); Paolo Cerasoli, San Giovanni Teatino (IT); Fabio Arrizza, San Giovanni Teatino (IT)

(73) Assignee: Glomeria Therapeutics S.R.L., San Giovanni Teatino (IT)

( * ) Notice: Subject to any disclaimer, the term of this patent is extended or adjusted under 35 U.S.C. 154(b) by 609 days.

(21) Appl. No.: 12/376,929

(22) PCT Filed: Aug. 13, 2007

(86) PCT No.: PCT/EP2007/058364
§ 371 (c)(1),
(2), (4) Date: Jul. 30, 2010

(87) PCT Pub. No.: WO2008/017727
PCT Pub. Date: Feb. 14, 2008

(65) Prior Publication Data
US 2010/0292633 A1    Nov. 18, 2010

(30) Foreign Application Priority Data

Aug. 11, 2006  (IT) ............................. RM2006A0444

(51) Int. Cl.
*A61M 25/16* (2006.01)
*A61M 25/18* (2006.01)
*A61M 5/00* (2006.01)
*A61M 25/00* (2006.01)

(52) U.S. Cl.
USPC ........................ 604/537; 604/248; 604/284

(58) Field of Classification Search
USPC ....... 604/164.11–167.05, 533–539, 248–256, 604/284; 137/556
See application file for complete search history.

(56) References Cited

U.S. PATENT DOCUMENTS

| 4,585,436 A * | 4/1986 | Davis et al. ....................... 604/29 |
| 4,821,996 A * | 4/1989 | Bellotti et al. ..................... 251/9 |
| 4,946,434 A * | 8/1990 | Plaisted et al. .................. 494/29 |
| 5,713,850 A * | 2/1998 | Heilmann et al. ............... 604/28 |

FOREIGN PATENT DOCUMENTS

| EP | 0715860 A | 6/1996 |
| EP | 1020203 A | 7/2000 |
| WO | 2005082437 A | 9/2005 |
| WO | 2006042016 A | 4/2006 |
| WO | 2006056827 A | 6/2006 |

* cited by examiner

*Primary Examiner* — Matthew F Desanto
(74) *Attorney, Agent, or Firm* — Lucas & Mercanti, LLP

(57) ABSTRACT

A coupling device (1) for the connection of two ends (3, 9) of respective tubular members (2, 5), allowing the contact of the flowing fluid only with elements inside a closed container, circumstances and an inherently easy connection operation, thus it can be carried out, comprising: a closed container (10) housing said ends (3, 9) of respective tubular members (2, 5), one of said tubular members having a flexible terminal section (8) thereof inside said closed container; a mobile connection member (15), coupled at the end of said flexible terminal section (8), having a nozzle (16) apt to be inserted within a receiving end of the other tubular member,—and a cam device, located inside said closed container (10) and apt to be actuated from the outside of said closed container, apt to cooperate with said mobile connection member (15), the cam device causing the insertion and the ejection of said nozzle in and from said receiving end, and the corresponding connection and the disconnection of the two ends.

17 Claims, 8 Drawing Sheets

COUPLING DEVICE AND USE THEREOF

This application is a U.S. national stage of PCT/EP2007/058364 filed on Aug. 13, 2007, which claims priority to and the benefit of Italian Application No. RM2006A000444, filed on Aug. 11, 2006.

The present invention is related to a coupling device, in particular for the connection of the ends of respective tubular members, for establishing a fluid communication through them.

The invention is also referred to the use of such a device, specifically for the joint of a catheter, introduced inside a living body, particularly a human body, to carry out, though said catheter and through the tubular member connected thereto, a treatment providing the extraction and/or the introduction of fluids from/into the living body.

A specific embodiment is constituted by the joint of a catheter introduced inside a human body for implementing a peritoneal dialysis. The catheter is provided with an extension suitable for carrying out said joint.

A noticeable drawback of the known devices is that the contact between the fluid passing through both the tubular members and through the related connection and surfaces, even of reduced area, previously exposed, even for very short periods, to the external environment is not prevented in an absolutely certain manner.

As it is apparent, such a contact could involve a contamination of the fluid which may thwart, in general terms, the purity or the full sterility of the fluid itself.

In particular, when one of the tubular members is a catheter, the contamination would lead to the extraneous, and possibly pathogenic, agent introduction inside the living body. In the case of peritoneal dialysis, the infectious agent introduction would lead to a dangerous peritonitis.

In the medical practice, to prevent any contamination, complex maneuverings are required, feasible by expert medical personnel. Where such competences are lacking, the connection operations cannot be carried out with the required clinical safety, in fact preventing the feasibility of such medical treatments outside medical facilities.

The technical problem underlying the present invention is to provide a coupling device allowing to obviate to the drawback mentioned above with reference to the known art.

Such a problem is solved by a coupling device for the connection of two ends of respective tubular members, comprising:
- a closed container housing said ends of respective tubular members, one of said tubular members having a flexible terminal section thereof inside said closed container;
- a mobile connection member, coupled at the end of said flexible terminal section, having a nozzle apt to be inserted within a receiving end of the other tubular member; and
- a cam device, located inside said closed container and apt to be actuated from the outside of said closed container, apt to cooperate with said mobile connection member, the cam device causing the insertion and the ejection of said nozzle in and from said receiving end, and the corresponding connection and the disconnection of the two ends.

The main advantage of the device according to the present invention lies in allowing the contact of the flowing fluid only with elements inside the closed container, packaged and prepared according to the caution required by specific circumstances, and with the internal surface of the receiving end tubular member, certainly excluding any other surface. The connection operation is inherently easy, thus it can be carried out by non-expert personnel.

In the case of medical treatments, the use of such a device permits the carrying out thereof also at home, the connection being actuatable by the patient, by a family carer or by a relative.

The present invention will be described hereinafter according to two preferred embodiment thereof, provided only to an exemplificative and non-limiting purpose with reference to the annexed drawings wherein.

Figure 1:
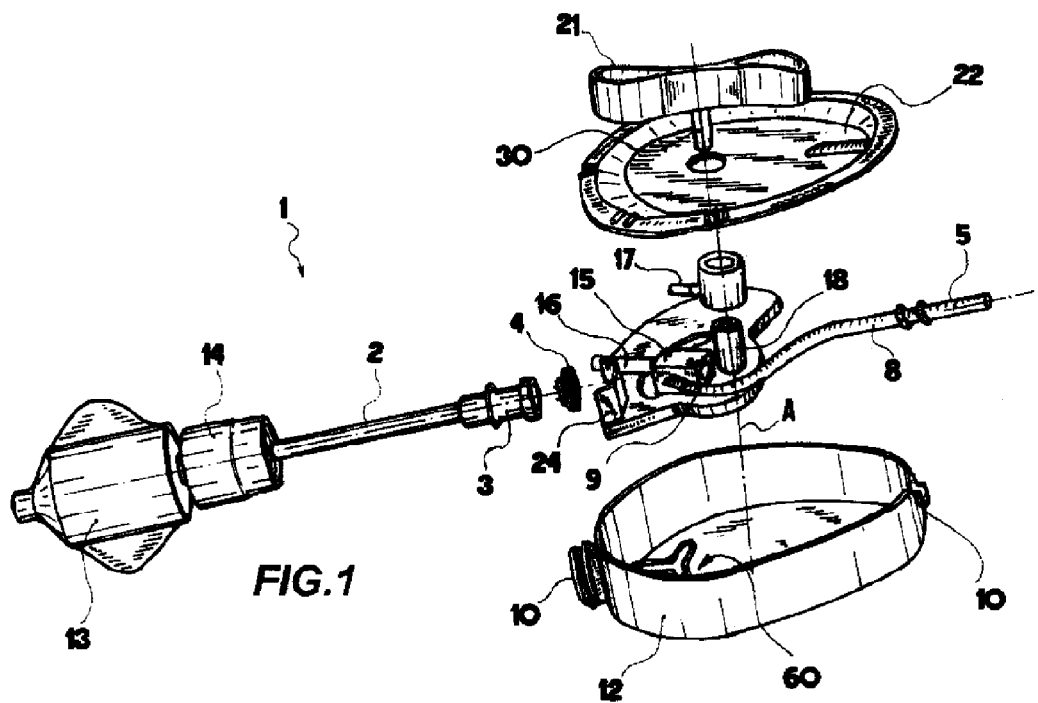
FIG. 1 shows an exploded perspective view of a coupling device of a first embodiment according to the invention.
Figure 2:
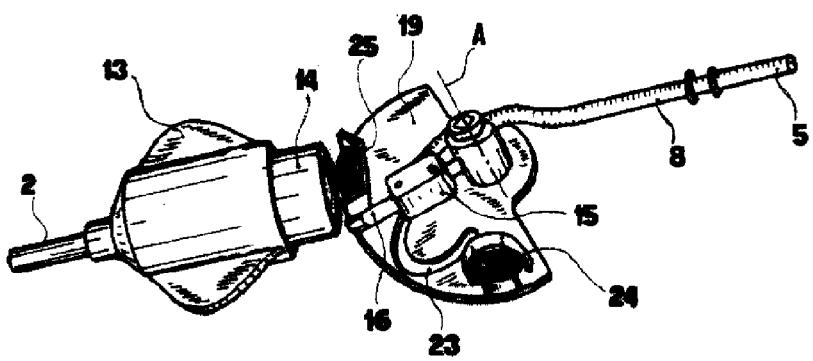
FIG. 2 shows a partial perspective view of the coupling device of FIG. 1.
Figure 3:
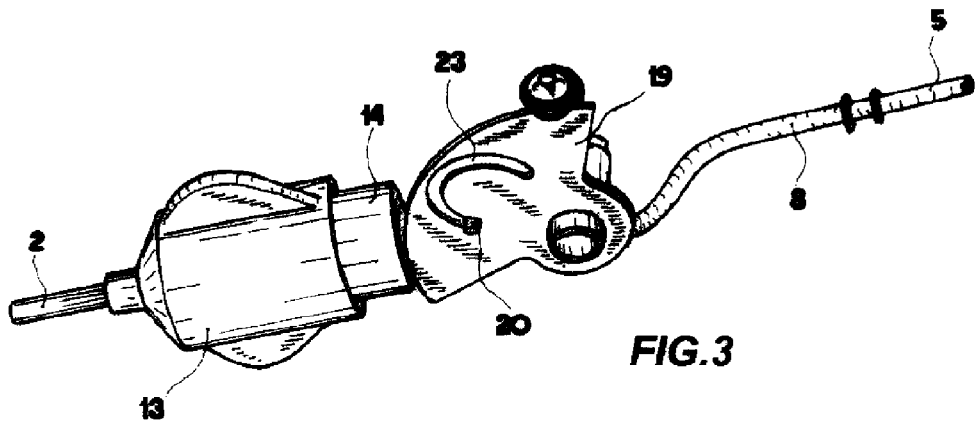
FIG. 3 shows a further partial perspective view of the coupling device of FIG. 1.
Figure 4:
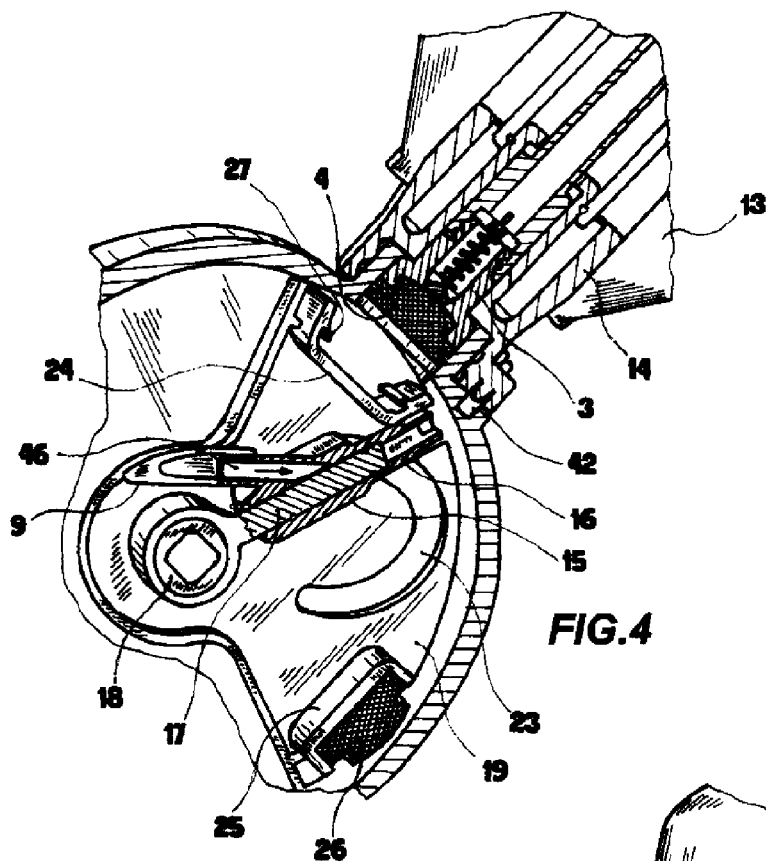
FIG. 4 shows an enlarged and sectioned perspective view of a detail of the device of FIG. 1 in a first operative configuration.

With reference to the figures, a coupling device is globally indicated as 1. It is intended for the connection of a pair of tubular members at respective terminal ends thereof.

In particular, a first tubular member is composed by the leg of a catheter 2, having a first connection end 3 with enlarged diameter, closed by a first cap member 4. Such first end will be also hereinafter identified with the term receiving end.

The coupling device 1 of this embodiment is intended for joining said first tubular member 2 with a second tubular member 5, e.g. a flexible pipe.

The second tubular member 5 has a flexible terminal section 8 in turn comprising a respective second connection end 9 which has to be connected to the above mentioned first connection end 3.

Particularly in the present embodiment, the second tubular member 5 is linked to a distribution and pump device for APD-type peritoneal dialysis (automated peritoneal dialysis), and the device 1 is used for joining such pump device (not represented) to the peritoneal catheter which is the first tubular member 2.

Then, the device comprises a closed container 10 housing said ends 3, 9 of respective tubular members 2, 5. The first end 3 is located at an opening 11 formed in a peripheral wall 12 of the container 10.

The closed container 10 is box-like and flattened, with a front wall 22 and a bottom wall, parallel to each other, joined by a peripheral wall.

At said opening 11, the device 1 comprises means for driving said connection end 3 comprising a sliding member 13 outside said closed container 10, substantially hood-shaped.

Such sliding member 13 is linked and integral to said first tubular member 2, at the receiving end 3 housed thereinto, being longitudinally passed through by the tubular member 2.

Between the sliding member 13 and the enlarged diameter receiving end 3 a coupling ring member 14 is provided, apt to be framed inside the sliding member 13 by means of a longitudinal prismatic guide (non represented). Therefore, the coupling ring member, intended to be rested at said opening 11, is apt to be secured to said closed container 10, in particular by means of a screw-type joint at said opening 11.

The coupling device 1 comprises a snap-action locking system for blocking the sliding member 13 to the closed container. Such a system is operated between the sliding member 13 and the coupling ring member 14 and comprises a snap-action locking pin 41 intended to be received in a pin seat 42 externally formed in the closed container 10 at said opening 11.

The locking pin 41 is inserted in an radially-projecting annular rim 43 of the coupling ring member 14 formed at the end thereof facing the closed container 10, intended to be put in contact with the closed container 10 and also embodying stop means of the sliding member 13. In such a way, the annular rim 43 is arranged between the closed container 10 and the sliding member 13.

The locking pin 41 has an opposite button end 44 externally projecting from the annular rim 43 in the direction of the sliding member 13, which is pressed thereby when the sliding member 13 is driven at the end of the travel thereof.

In such a way, the locking pin 41 is pushed, being thereby inserted in the seat 42 thereof on the closed container, hence preventing the unscrewing of the coupling ring member 14. A further pressing of the sliding member 13 on the button end 44 results in a retraction of the pin 41 from the seat 42 thereof, thereby allowing the unscrewing. The extension-retraction movement is caused by a snap action spring-mechanism (not shown in the figures) embedded into the annular ring and driven by the sliding of the sliding member 13. The assembly formed by the sliding member 13, the coupling ring member 14 with its annular ring 43 and the locking pin 41 results in a snap-action locking system for the sliding member 13 bearing the receiving end 3 of the catheter 2, apt to secure the latter to the container 10 and insert the receiving end 3 therein.

The second end 9 is coupled to an elongated mobile connection member 15 having a fluid path longitudinally formed therein. It has a pin-shaped nozzle 16, apt to be inserted into the receiving end 3 of the other tubular member 2.

Said connection member 15 slides along a stem 17 placed inside an appropriate axial hole 45 of the connection member 15. One proximal end of the this stem 17 is articulated at a first hinge pin 18, embodying a rotation axis A which will be described hereinafter in more detail.

In such a way and in general the mobile connection member 15 is intended to be moved along circumferential paths, around the first hinge pin 18, and radial paths, along the stem 17, or combinations thereof.

In detail, the axial hole 45 longitudinally extends in the mobile connection member 15 from one end to the other and through the nozzle 16, and a connection branch 46 laterally projects from the connection member 15 forming a projecting outlet to which the terminal end 9 of the second tubular member 5 can be secured, e.g. it can be externally fitted. Along the connection branch 46 a branch hole is formed, opened into the axial hole, thereby putting into fluid communication the second tubular member 2 and the axial hole 45, i.e. the nozzle 16 intended to be inserted into the receiving end 3 of the first tubular member 2.

The stem 17 is provided with spaced seal rings 47. The mobile connection member 15 can be moved along the stem 17 from a proximal position, wherein the connection member 15 is at the hinge pin 18 and wherein the stem 17 with the seal ring 47 act as shutter for the fluid path inside the connection member 15, letting the branch hole of the connection branch 46 to be shut.

In particular, the stem 17 has at least two spaced seal rings 47 and, when the connection member is in the proximal ends thereof with respect to the hinge pin 18, the mouth of the branch hole is arranged between said seal rings 47.

In the opposite distal position, far away from the hinge pin 18, the connection member 15 has the nozzle 16 thereof inserted into the receiving end 3. In this configuration, the stem 17 is retracted inside the axial hole 45 with respect to the mouth of the branch hole, leaving open the fluid path from the second tubular member 5 to the first tubular member 2.

The nozzle 16, at a resting end 48 thereof intended to be rested on a corresponding stop edge 72 in the receiving end 3, has side apertures 49. On such a resting end 48 a deformable bushing 50 is provided, acting as a sealing member and covering said side apertures 49 when the nozzle 16 is not inserted into the receiving end 3. When the nozzle 16 is inserted, the bushing 50 is compressed, leaving uncovered said side apertures 49. In general, the bushing 50, or another sealing member, is intended to produce a sealing in cooperation with said stop edge 72.

Then, the device 1 comprises a cam device for driving said mobile connection member 15. To this purpose, the connection member 15 has a driving pin 20 projecting between the connection member 15 and a bottom wall of the closed container 10, intended to operate as a cam follower.

The task of the cam device is to drive the connection member 15, first from a starting position wherein the nozzle 16 is coaxial with the receiving end 3, then in a position wherein the connection member 15 and the nozzle 16 are driven for the insertion into the receiving end 3, and then in a position wherein the connection member is retracted, resulting in the disconnection of the nozzle 16.

The cam device comprises a first cam profile member 19, inside said closed container 10 and driven from the outside of said closed container 10, so as to cooperate with said connection member 15, in particular with said driving pin 20 projecting from the connection member 15.

The first cam profile member 19 comprises a plate on which a first curved cam guide is formed, cooperating with the pin 20. The plate can be rotated around said rotation axis A by a knob 21 placed outside, on a front wall 22 of said closed container 10. The driving stem 30 of the knob 21 is inserted in a respective driving seat 31, axially formed into said hinge pin 18.

In the present embodiment, the first cam guide is a groove 23 receiving said pin 20, formed by a passing through notch into said plate. It is noted that the notch extends along a U-shaped curve, having the apex faced to the wall of the closed container 10 wherein said opening 11 is formed.

In the present embodiment intended for the medical use, the plate, i.e. the first cam profile member 19, rotated by the knob 21, can be rotated along only one direction (counter-clockwise) due to a non-return system (not shown), e.g. a plurality of teeth preventing the counter rotation of the plate 19. Thus, when the device has been used, it cannot be further used. Hence, it can be considered as a single use device.

The cam device further comprises a second cam profile member interacting with the preceding one. In the present embodiment, such second cam profile member comprises a second cam guide 60 formed into the surface of the closed container wall on which said first cam profile member 19 is rested. Since this cam guide is formed in a container wall, it can be considered a fixed cam guide, in opposition to the mobile cam groove 23.

Inside such second guide 60, a projecting pin 61 of said driving pin 20 is inserted, acting as a further guidance.

The second guide cam 60 has a first circumferential section 62, corresponding to the travelling path of the connection member 15 from the starting position to the insertion position, a second radial section 63, corresponding to the travelling path for the insertion and the disconnection of the nozzle 16 to and from the receiving end 3, a third circumferential section 64, corresponding to the travelling path from the disconnection position to the final position.

The sections 62, 63, 64 substantially form a Y-shaped guide, with the two arms curved. Said two circumferential sections 62, 64 are staggered, so as to result in a step 65 corresponding to the starting position.

As it will become apparent from the following description of the present embodiment, the rotation of the first cam profile member 19 with respect to the second cam guide 60 is such to result in the insertion and the disconnection of said nozzle 16 into and from said receiving end 3, determining the coupling of the ends 3, 9 of the tubular members 2, 5.

The first and the second cam profile members act together as a positively actuated gear, i.e. a desmodromic mechanism.

The device 1 comprises catching means for the cap member 4 closing the receiving end 3. Such catching means are composed by said first cam profile member 19, wherein a pair cap seats are formed.

Said plate is substantially circle shaped and the edge thereof remains adjacent to the peripheral wall of the closed container 10 in the rotation of the plate itself.

In particular, the plate embodying the first cam profile member 19 comprises a first cap seat 24, apt to receive the respective cap member 4 of the receiving end 3 in a position of the first cam profile member preceding the insertion position of the nozzle 16 into the receiving end 3. Said cap seat 24 substantially is a cup-shaped catching recess, integral to the plate embodying the cam profile and formed at the edge of the plate.

The first cam profile member 19 comprises then a second cap seat 25 receiving a further cap member 26, protected by the closed container 10. The seat 25 is positioned at said receiving end 3 once the disconnection of the nozzle 16 from the receiving end 3 has been completed.

Figure 11A:
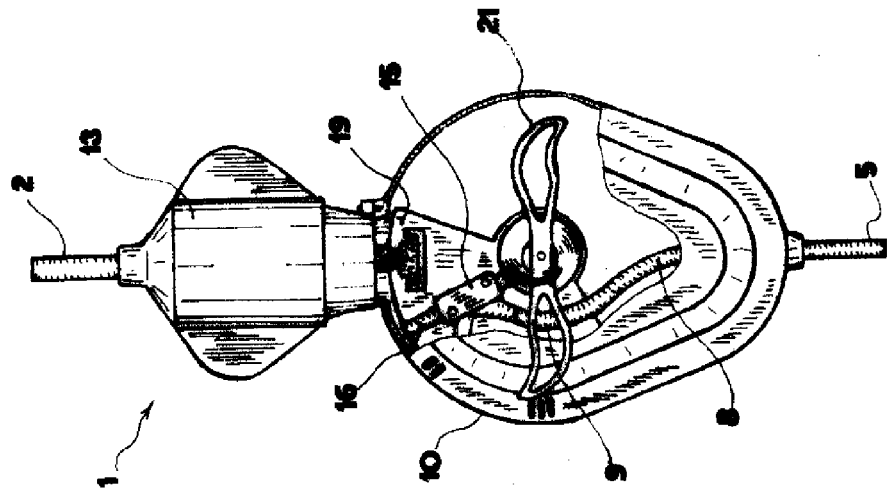
FIGS. 11A, 11B and 11C show a top plan view of the sectioned device of FIG. 1, so as to illustrate different operative configurations.

As a matter of fact, the first cam profile member 19 can be rotated from a first position (FIG. 11A) wherein the first seat 24 is arranged at said receiving end 3, and a final position (FIG. 11C) wherein said second seat 25 is arranged at said receiving end 3, passing through an intermediate position (FIG. 11B) wherein, due to the cam profiles, the nozzle 16 is inserted into said receiving end 3.

The first cap seat 24 of the catching means has a circumferential fin 27 intended to be framed into a corresponding peripheral groove 28 of each cap member. In such a way, the catching of the first cap member 4 occurs in a click by means of elastic interference between the cap member 4 and the fin 27.

The second seat 25 is lacking in a fin. It embodies release means of a further cap member 26 for closing the receiving end 26.

Figure 5:
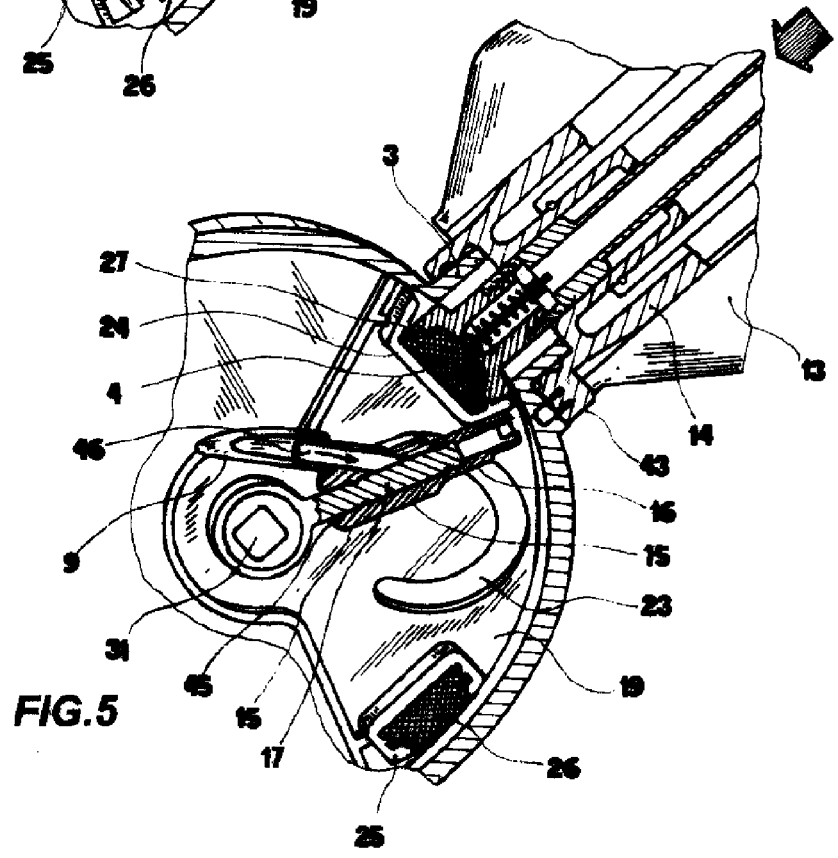
FIG. 5 shows the view of FIG. 4 with the device in a second operative configuration.

At the receiving end 3, a shutter device 70 is provided, comprising a shutter member 71 acting on the stop edge 72 inside the end 3, on which also the cap member 4 is rested (FIG. 5), mounted on a shutter stem 73 sliding inside a ring 74 secured inside the respective tubular member 2.

In the present embodiment, between shutter member 71 and the ring 74 a helical spring 75, coiled around the shutter stem 73, is provided, assuring the adhesion between shutter member 71 and respective stop edge 72.

In normal conditions, the shutter device acts as a check valve, preventing the leaking of the fluid inside the tubular member 2, regardless the presence of the plug 4. In such a way, the accidental loss of the cap member does not constitute an immediate problem.

Figure 7:
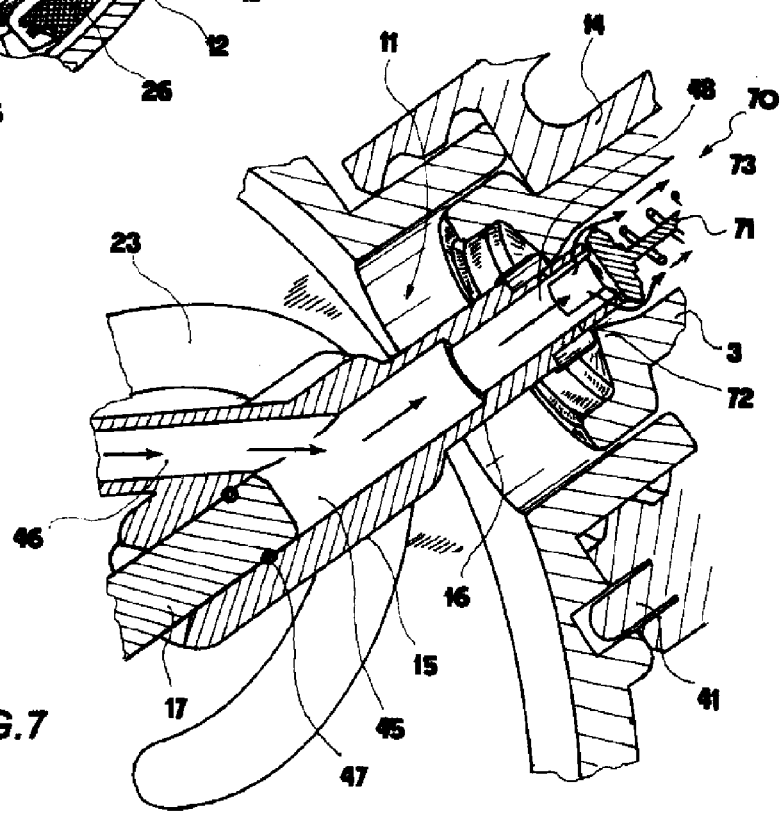
FIG. 7 shows the view of FIGS. 4 to 6 further enlarged, with the device in a fourth operative configuration.
Figure 8:
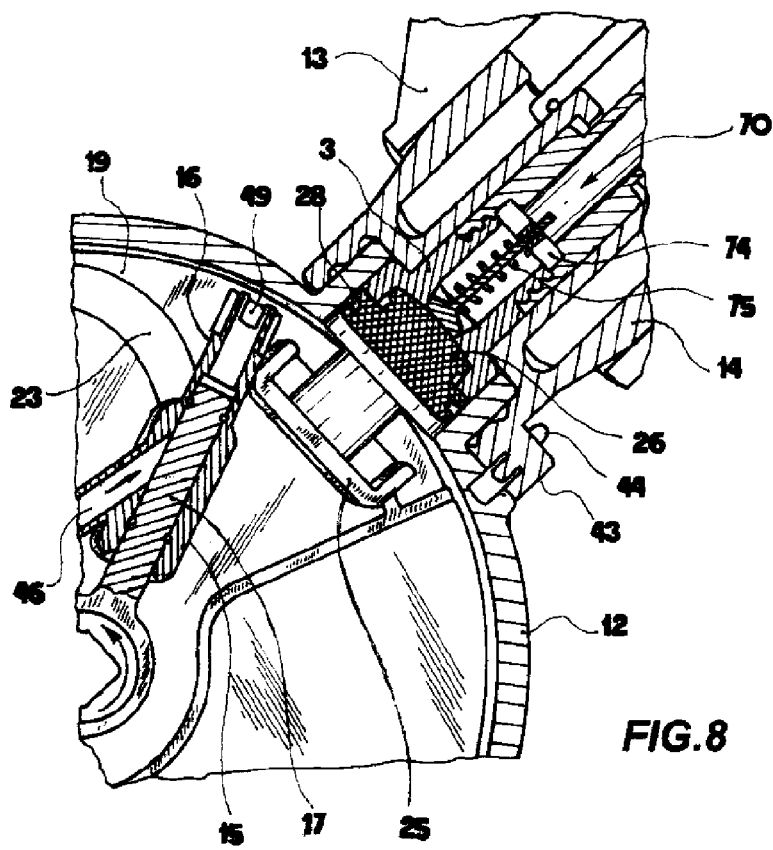
FIG. 8 shows the view of FIG. 7 with the device in a fifth operative configuration.
Figure 9:
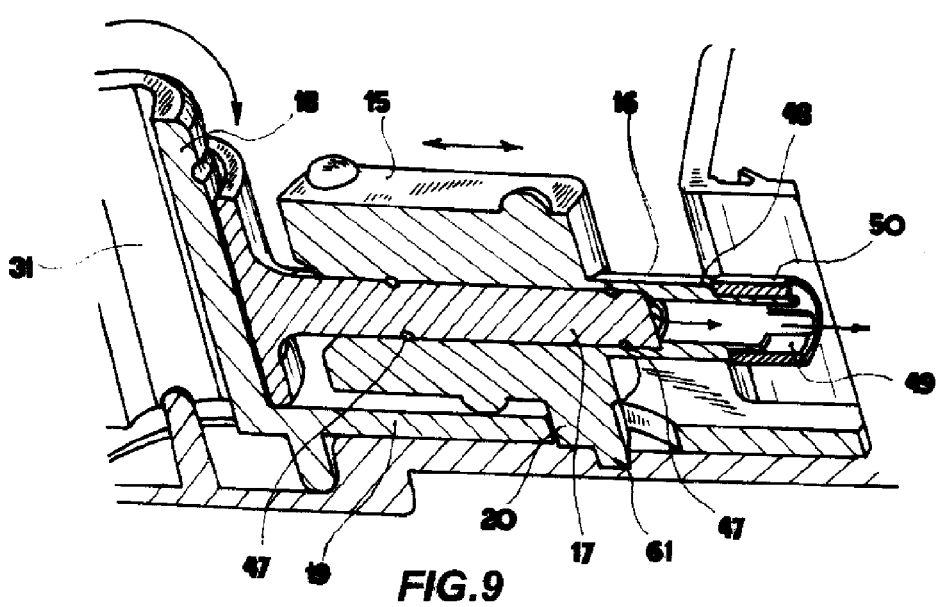
FIG. 9 shows a section of the further enlarged detail of the device of FIG. 1.
Figure 10A:
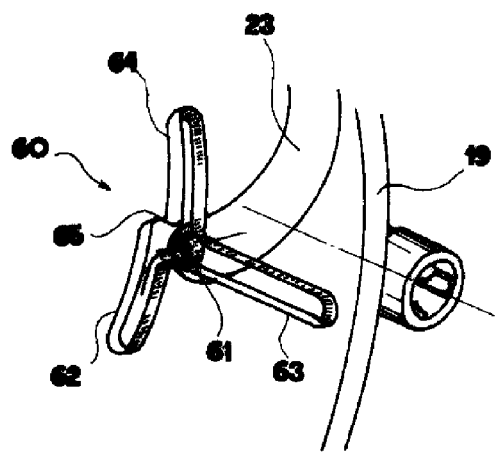
FIGS. 10A, 10B and 10C show schematic perspective views of an enlarged detail of the device of FIG. 1, in three different operative configuration, not visible in the preceding figures.
Figure 10B:
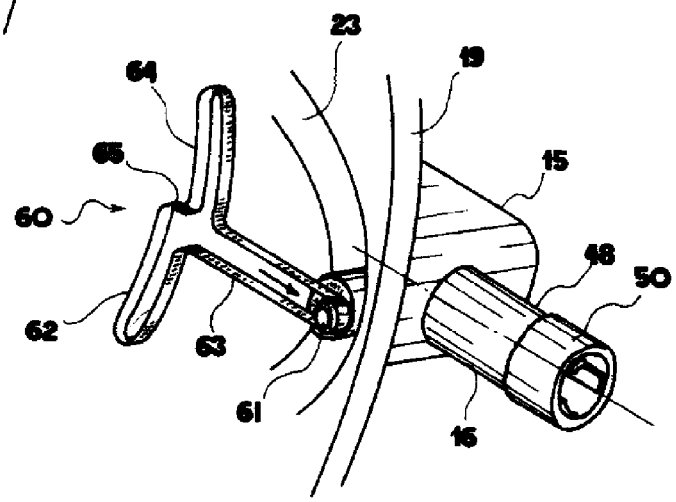
Figure 10C:
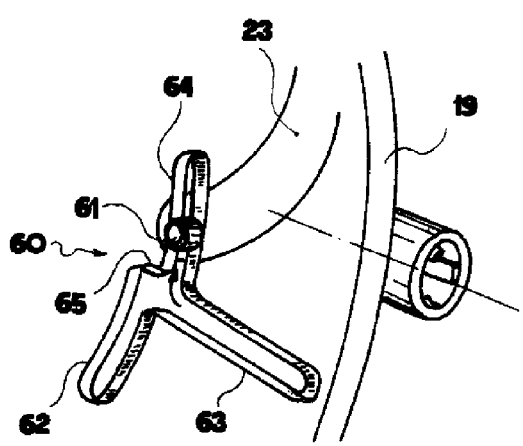

When the nozzle 16 is inserted into the receiving end 3, the resting end 48 thereof push inside the shutter member 71, against the spring force, while the sealing bushing 50 is compressed by the edge 72, leaving the corresponding side apertures 49 uncovered. In such a way, the fluid can flow through the receiving end 3 in both the directions (FIG. 7).

In connection with the operation of the device 1, it is arranged with the flexible section 8 of the second tubular member 5 inside the closed container 10, with the terminal end 9 fitted to the connection member 15 at said connection branch 46. The device 1, in the present embodiment, is provided to connect an APD-type dialysis unit to a peritoneal catheter, i.e. the first tubular member 2.

The latter has the enlarged diameter connection end 3, with the sliding member 13 and the coupling ring member 14. Turning the sliding member 13, the coupling ring member is screwed at the opening 11, placing the receiving end 3 in the correct position for the insertion of the nozzle 16.

Now, the sliding member 13 is moved toward the device, displacing the receiving end to drive the respective cap member 4 inside the first cap seat 24, resulting in the catching of the cap member 4 by means of the fin 27.

Figure 6:
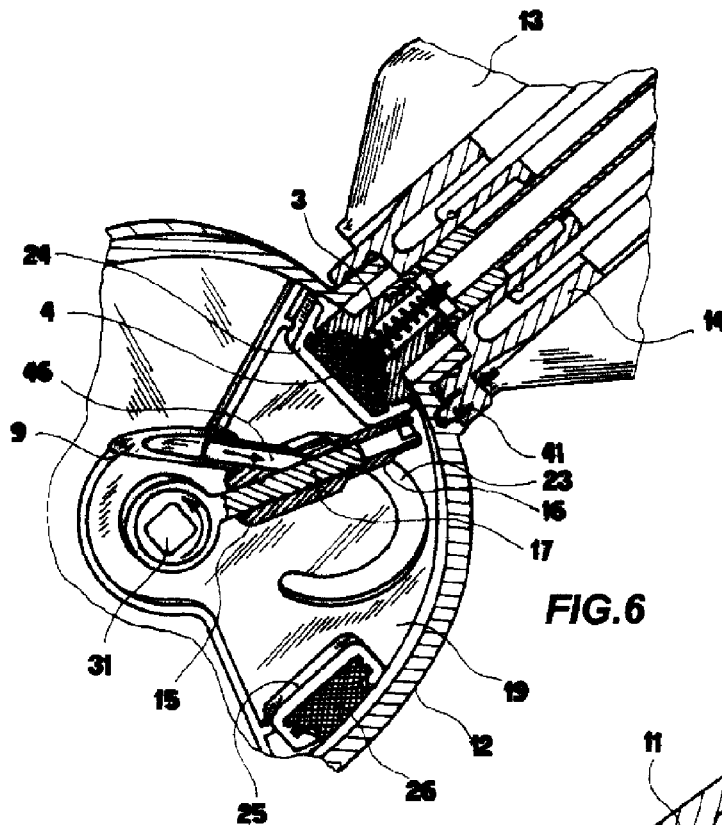
FIG. 6 shows the view of FIGS. 4 and 5 with the device in a third operative configuration.

Such a movement also results in the insertion of the locking pin 41 inside the locking seat 42 (FIG. 6).

The sliding member 13, and hence the end 3 of the catheter 2, is returned in the starting position thereof. To this purpose, such a return may be helped by a resilient member, like a helical spring (not shown) placed between the sliding member 13 and the coupling ring member 14.

Now, the knob 21 is rotated. The cam profile of the first cam profile member 19 acts on the driving pin 20 of the mobile connection member 15, letting the projecting pin 61 to proceed along the groove of the first section 62 of the second cam profile member 60, resulting in the positioning of the nozzle 16 coaxial to the receiving end 3.

A further rotation of the knob 21 results in the sliding of the mobile connection member 15 along the second radial section 63 of the second cam profile member 60, pushed by the curved profile of the groove 23. In such a way the insertion of the nozzle 16 into the receiving end 3 is obtained.

In the device, the position of the first cam profile member 19 and of the related knob is detectable outside the closed container 10 by a graduated scale I-II-III, preferably provided with relieved indicators for the tactile perception.

Figure 11B:
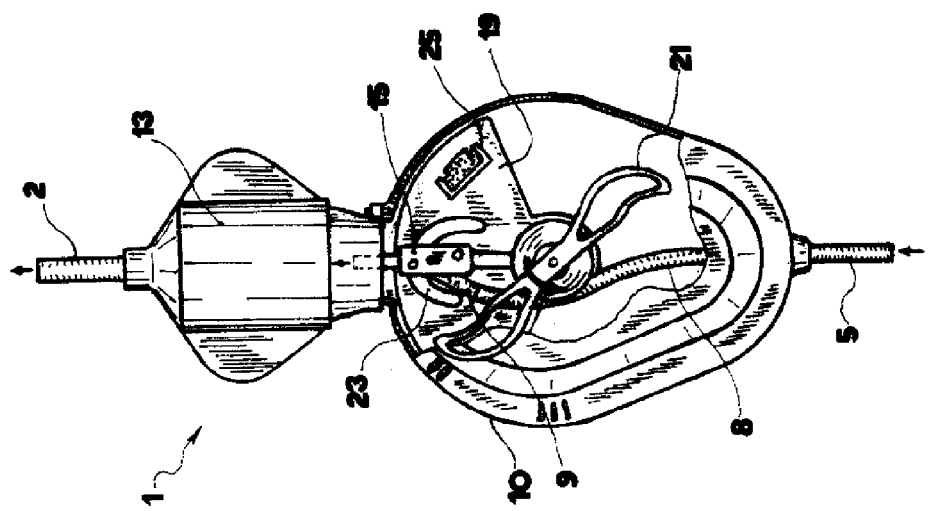

The insertion position is indicated by the intermediate indicator II (FIG. 11B).

Figure 11C:
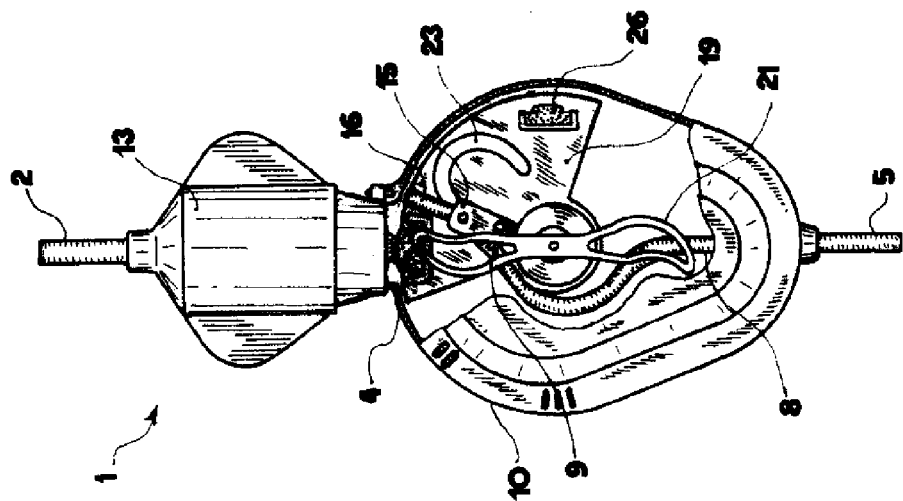
Figure 12:
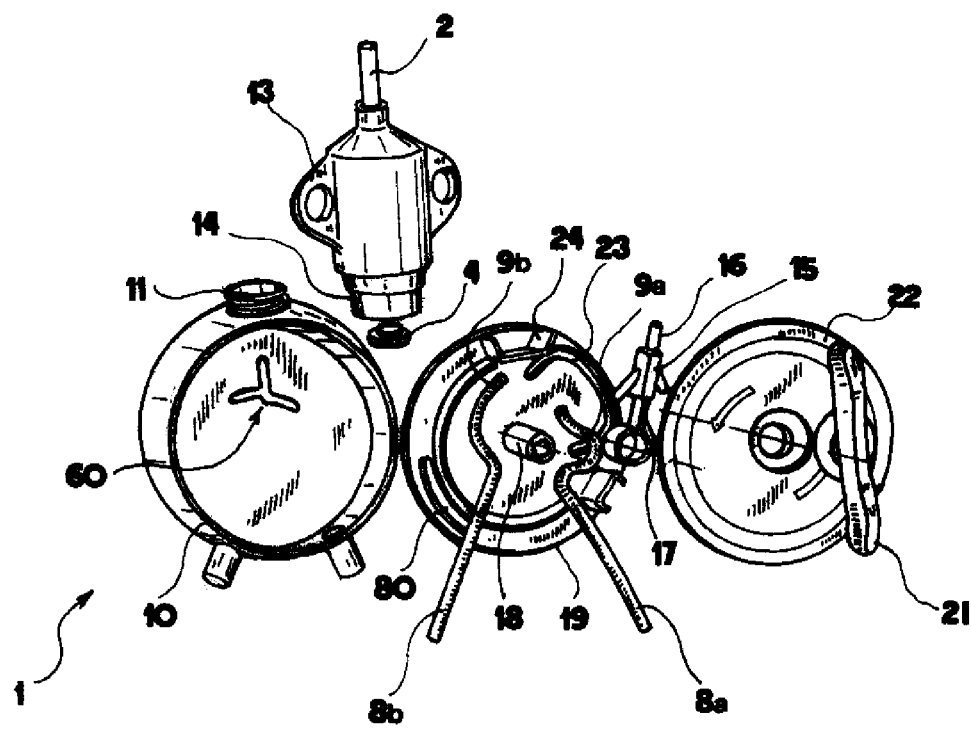
FIG. 12 shows an exploded perspective view of a coupling device of a second embodiment according to the invention.

When the connection has to be concluded, the knob 21 is rotated along the same counter-clockwise direction to the end position thereof (indicator III. FIG. 11C). The connection member 15 is retracted along the third radial section of the second cam profile member 60, and then translated along said third circumferential section 64. In this way, at the end the second cap member 26 is positioned in front of the receiving end 3.

Lowering the sliding member 13, the receiving end 3 is moved ahead to catch the cap member 26, resulting in the closure of the catheter 2 until the next application.

Such a lowering causes the snap-action and the consequent retraction of the locking pin 41, allowing the unscrewing and the separation of the coupling ring member 14.

Therefore, it is intended that in a clinical environment and in particular for peritoneal dialysis treatments, the device 1 is of the single-use-type, sold in a kit comprising the above device, a positive displacement (volumetric) diaphragm pump and the connection lines to the solution and discharge bags (not shown).

Figure 13:
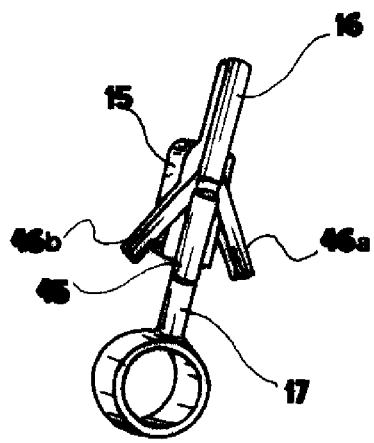
FIG. 13 shows a sectioned perspective view of a detail of the device of FIG. 13.
Figure 14:
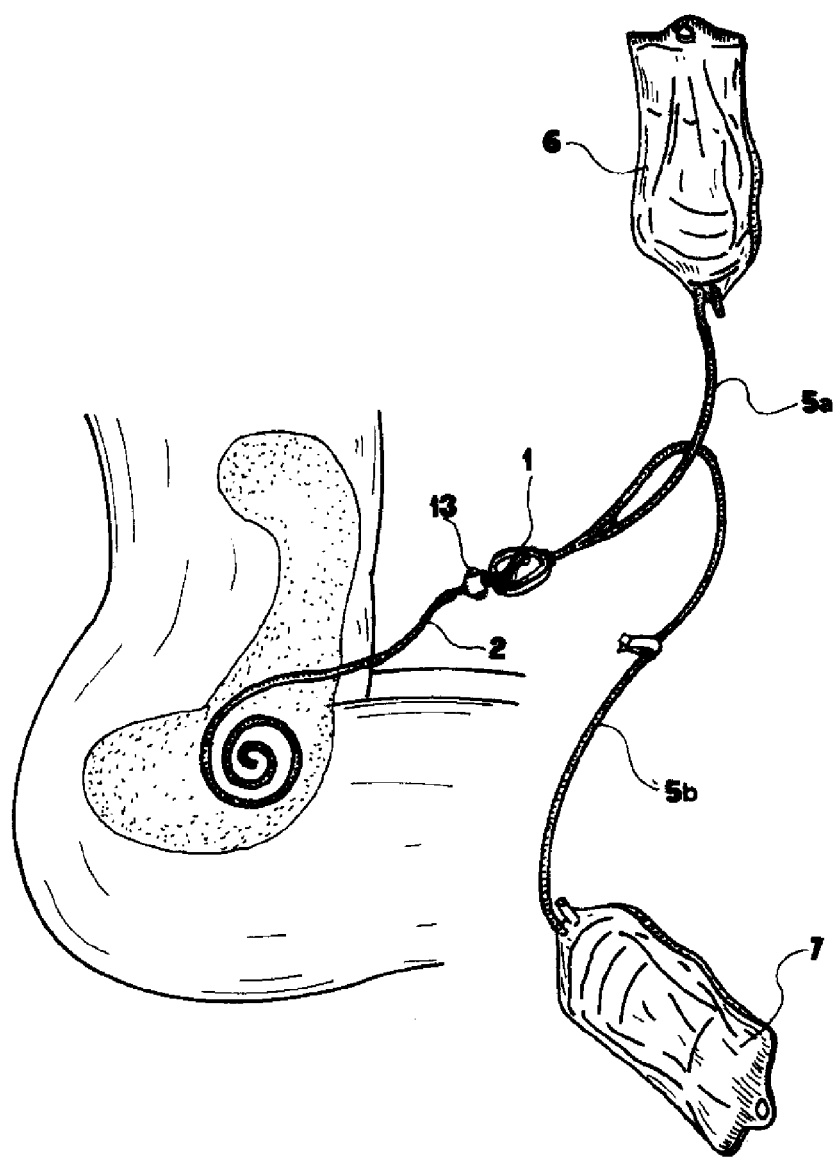
FIG. 14 shows a view illustrating the use of the device of FIG. 13 in a medical environment, related to a CAPD-type peritoneal dialysis.

With reference to FIGS. 13 to 15, a second embodiment of the coupling device according to the invention is disclosed, substantially analogous to the preceding one. In the drawings, the same previously cited numeral references are used for identifying same or analogous parts.

The device 1 of the second embodiment comprises a container 10 closed by a wall 22 with a knob 21, rotating a first cam profile member 19. The later cooperates with a second cam profile member 60 formed in the inner surface of the bottom wall of the closed container 10.

A stem 17 is rotatably hinged around a hinge pin 18, the stem 17 being inserted through the axial hole 45 of a connection member 15, provided with a pin-type nozzle 16 intended to be inserted into a receiving end 3.

In this embodiment, the device I suitable for joining the receiving end 3 of a peritoneal catheter 2 alternatively to two different flexible pipes 5a and 5b, both comprising a flexible terminals section 8a and 8b with respective connection end 9a, 9b.

The two flexible pipes are connected to a dialysis solution bag 6, placed in a raised position and containing a dialysis solution to be injected into the human body inside the peritoneum, and to a discharge bag 7, positioned in a lowered position and intended to receive the exhausted discharge solution, respectively.

This configuration realizes the so-called CAPD-type peritoneal dialysis (continuous ambulatory peritoneal dialysis).

Hence, the device 1, connected to the peritoneal catheter through a suitable connection assembly (not shown), first connects the catheter 2 to the dialysis solution bag 6, from which the dialysis solution is driven by gravity into the human body, and then it connects the catheter 2 to the discharge bag 7, to which the exhausted solution is driven by gravity. The device 1 is therefore alternatively passed through by fluids according to two contrary directions.

The cam guide 23 of the first cam profile member 19 is again U-shaped, but it comprises a central circumferential section.

When the first cam profile member 19 is rotated from a first insertion position, the connection member 15 remains with the nozzle 16 inserted into the receiving end 3 until the end of such circumferential section, and another further rotation causes the disconnection. Therefore, four positions are provide, indicated as I-II-III-IV by suitable indicators on the wall 22 in connection with the knob 21.

The connection member 15 is provided with two connection branches 46a and 46b, respectively joined to the second connection ends 9a, 9b. They are closed and opened by the relative movement of the stem 17 (FIG. 14). In particular, they are opened when the nozzle 16 is inserted into the receiving end 3 (positions II and III).

On the first cam profile member 19 and on the back of the wall 22 (not visible), means for selectively blocking the flexible sections 8a, 8b, comprising relieved profiles 80 squeezing, according to the position of the first cam profile member 19, said sections 8a, 8b.

In connection with the operation of the present device, it is analogous to that previously described, but in position II the second flexible section 8b is squeezed, allowing only the passage of the solution from the solution bag 6 through the catheter.

When the dialysis solution bag 6 is emptied, and after a predetermined length of time, the knob is rotated into position III, determining the opening of the previously squeezed second flexible section 8b, but squeezing the first flexible section 8a. According to this arrangement, the exhausted solution is allowed to flow into the discharge bag 7. At the end of this process, the knob 21 is rotated until position IV, and hence the catheter is closed by the second cap member 26. Then the device 1, together with the kit comprising the flexible pipes 5a, 5b and the bags 6, 7 can be disposed.

It is intended that, according to a possible modification, the two branches are selectively opened or closed.

To the above disclosed coupling devices a man skilled in the art, to meet further and specific needs, may achieve several additional variations, in any case all embraced by the protection scope defined by the annexed claims.

The invention claimed is:

1. Coupling device for the connection of two ends of respective tubular members, comprising:
   a closed container housing said ends of respective tubular members, one of said tubular members having a flexible terminal section thereof inside said closed container;
   a mobile connection member, coupled at the end of said flexible terminal section, having a nozzle apt to be inserted within a receiving end of the other tubular member; and
   a cam device, located inside said closed container and apt to be actuated from the outside of said closed container, apt to cooperate with said mobile connection member, the cam device causing the insertion and the ejection of said nozzle in and from said receiving end, and the corresponding connection and the disconnection of the two ends;
   wherein
   said cam device comprises a fixed cam guide; and said cam guide has a first circumferential section, corresponding to the travelling path of the connection member from a starting position an insertion position, a second radial section, corresponding to said travelling path for the insertion and the disconnection of the nozzle, a third circumferential section, corresponding to said travelling path from the disconnection position a final position, the sections substantially forming a Y-shaped guide, with the two arms of the Y curved.

2. Coupling device according to claim 1, wherein said cam device comprises a cam profile member rotating around an axis and rotated by a knob arranged outside a wall of said closed container.

3. Coupling device according to claim 2, wherein the mobile connection member can slide along a stem, one end thereof being hinged with respect to the rotation axis of the cam profile member, the stem passing through a suitable axial hole of the mobile connection member.

4. Coupling device according to claim 3, wherein said axial hole longitudinally extends between the ends of the mobile connection member and the nozzle, and at least one connection branch projects from the mobile connection member so as to be secured to the terminal end of the second tubular member.

5. Coupling device according to claim 4, wherein the stem is provided with seal rings and acts as a shutter for the fluid path inside the mobile connection member, letting a branch hole in the of the connection branch to be shut.

6. Coupling device according to claim 2, wherein said cam profile member comprises a plate on which a curved cam guide is formed, cooperating with a pin of said mobile connection member.

7. Coupling device according to claim 6, wherein said fixed cam guide is formed into a surface of a wall of the closed container and a projection, acting as a cam follower, of said pin is inserted into said fixed cam guide.

8. Coupling device according to claim 1, including means for driving said terminal receiving ends and means for catching and releasing a cap member closing said receiving end, cooperating to each other for opening and closing the receiving end.

9. Coupling device according to claim 8, wherein said cam profile member comprises a plate on which a curved cam guide is formed, cooperating with a pin of said mobile connection member, and said means for catching and releasing comprises one or more cap seats formed in said plate.

10. Coupling device according to claim 9, wherein said plate comprises:
   a first cap seat, apt to receive a respective cap member of the terminal receiving end in a position of the plate preceding the insertion of the nozzle;
   a second cap seat receiving a further cap member, protected by the closed container, positioned at said terminal receiving end once the disconnection of the nozzle from the terminal receiving end has been completed.

11. Coupling device according to claim 8, wherein said means for driving comprises a sliding member outside said closed container and joined to a respective tubular member at the receiving end.

12. Coupling device according to claim 1, wherein said fixed cam guide is formed into a surface of a wall of the closed container.

13. Coupling device according to claim 1, wherein said two circumferential sections are staggered, so as to result in a step corresponding a starting position.

14. Coupling device according to claim 1, wherein the nozzle has side openings at a resting end thereof intended to be rested on a corresponding stop edge of the receiving terminal end.

15. Coupling device according to claim 1, wherein, at the terminal receiving end, a shutter device is provided, comprising a shutter member acting on a stop edge of the respective tubular member inside the terminal receiving end, mounted on a shutter stem sliding inside a ring secured inside the respective tubular member, thereby acting as a check valve, preventing the leaking of the fluid inside the respective tubular member.

16. Single use disposable kit for peritoneal dialysis, including a coupling device of claim 1, connection pipes and at least one pump device for an APD-type peritoneal dialysis.

17. Single use disposable kit for peritoneal dialysis, including a coupling device of claim 1, a dialysis solution bag with a suitable dialysis solution, a discharge bag for the exhausted solution and related connection pipes for a CAPD-type peritoneal dialysis.

* * * * *

UNITED STATES PATENT AND TRADEMARK OFFICE
CERTIFICATE OF CORRECTION

PATENT NO. : 8,518,015 B2
APPLICATION NO. : 12/376929
DATED : August 27, 2013
INVENTOR(S) : Arduini et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1149 days.

Signed and Sealed this
Fifteenth Day of September, 2015

Michelle K. Lee
*Director of the United States Patent and Trademark Office*